United States Patent [19]

Neufeld et al.

[11] Patent Number: 4,760,020

[45] Date of Patent: Jul. 26, 1988

[54] METHOD FOR TESTING BIOCOMPATIBILITY

[75] Inventors: Arthur H. Neufeld, Newton Highlands; Marcia M. Jumblatt, Swampscott, both of Mass.

[73] Assignee: Eye Research Institute of Retina Foundation, Boston, Mass.

[21] Appl. No.: 730,671

[22] Filed: May 3, 1985

[51] Int. Cl.$^4$ ............................ C12Q 1/02; C12N 5/00
[52] U.S. Cl. .................................... 435/29; 435/240.2; 436/63
[58] Field of Search ...................... 435/29, 240, 240.2; 436/63

[56] References Cited

PUBLICATIONS

Push, "Scientists Eye Draize Test Alternatives" The John Hopkins Center for Alternatives to Animal Testing Newsletter, vol. 3, No. 1, pp. 1–8 (1984).
Dagani, "In-Vitro Methods May Offer Alternatives to Animal Testing" C & EN (Nov. 12, 1984) pp. 25–28.
Jumblatt et al., "A Tissue Culture Model of Ocular Irritancy" ARVO Abstract (1984).
Jumblatt & Neufeld, "Corneal Epithelial Wound Closure: A Tissue Culture Model" ARVO Abstracts, May 1–May 6, (1983).
Ubels et al., "Healing of Experimental Corneal Wounds Treated With Topically Applied Retinoids", Am. J. Opthalmol. 95:353–358 (1983).
Dagani, "Alternative Methods Could Cut Animal Use in Toxicity Tests" C & EN Oct. 31, 1983, pp. 7–13.
Jumblatt & Neufeld "B–Adrenergic and Serotenergic Responsiveness of Rabbit Corneal Epithelial Cells in Culture", Invest. Opthalmol. Vis. Sci. 24:1139–1143 (1983).
Falahee et al. "Eye Irritation Testing: An Assessment of Methods and Guidelines for Testing Materials for Eye Irritancy" EPA–560/11–82 001 Oct. (1981).
Gipson et al. "Effects of Cytochalasins B & D and Colchicine on Migration of the Corneal Epithelium" Invest. Opthalmol. Vis. Sci. 22:633–642 (1982).
Gipson & Anderson "Effect of Lectins on Migration of the Corneal Epithelium" Invest. Opthalmol. Vis. Sci. 19:341–349 (1980).
Thompson et al. "The Effect of An Eye Derived Growth Factor (EDGF) on Corneal Epithelial Regeneration: Exp. Eye Res. 34:191–199 (1982).
Jumblatt et al. "Cholera Toxin Stimulates Adenosine 3'5' Monophosphate Synthesis and Epithelial Wound Closure in the Rabbit Cornea" Invest. Opthalmol. Vis. Sci. 19:1321–1327 (1980).
Jumblatt and Neufeld "Characterrization of Cyclic AMP-mediated Wound Closure of the Rabbit Corneal Epithelium" current Eye Res. 1:189–195 (1981).
Cintron et al. "A Simple Method for the Removal of Rabbit Corneal Epithelium Utilizing n—Heptanol" Opthalmic Res. 11:90–96 (1979).
Jumblatt & Neufeld "A Tissue Culture Model of the Human Corneal Epithelium" (Opthalmic Pharmacology Unit Eye Research Institute & Dept. of Opthalmology Harvard Medical School, Boston, Mass.

Primary Examiner—Esther M. Kepplinger
Attorney, Agent, or Firm—Lahive & Cockfield

[57] ABSTRACT

An in vitro testing method for biocompatibility, particularly toxicological effect, of substances is based on the change in the time for closure of a disruption in a confluent cell culture caused by treatment with the substance. The method can be used to replace a substantial number of toxicity tests, including the Draize test for ocular irritancy.

13 Claims, 1 Drawing Sheet

METHOD FOR TESTING BIOCOMPATIBILITY

BACKGROUND OF THE INVENTION

A large number of diverse products, including drugs, aerosols, household products, and cosmetics, are presently tested for biocompatibility. Biocompatibility, which embraces positive or compatible reactions and negative or toxcological effects, is a term used to describe a wide range of reactions with biological, particularly mammalian, tissue. In fact, many products which can come in contact with eyes, skin, mucous membranes, or other organs are routinely tested for biocompatibility. Contact with these materials may be initiated by a variety of means, such as topical application, inhalation, or ingestion.

The United States Food and Drug Administration, as well as other governmental agencies, request that manufacturers supply information on biocompatibility, particularly toxicological effects, on most products which may come accidently or intentionally into contact with eye, skin or mucous membranes. The protocols for many biocompatibility tests require the use of live animals. Many conventional tests for biocompatibility cause rashes or other irritations of the skin, mucous membranes and ocular tissue on the test animal. Public concern over the use of live animals in research, as well as in biocompatibility testing, is one problem which has led to a search for alternative test methods. Other problems are that these standard procedures for testing are subjective, not easily quantified and do not always mimic the effects on humans; rather, the procedures are used because they show an easily identifiable, high level response.

The Draize test, which is used to determine the toxicological effect of a variety of substances including cosmetics and household products on eyes, is one test which has been criticized. In the standard Draize test, the substance to be tested is placed into the lower conjunctival sac of rabbit eyes and the eyes are monitored for extent and duration of injury. The Food and Drug Administration has suggested a modified Draize test as the preferred method of eye irritancy evaluation (Federal Hazards Substances Act (1964)). This modification uses six rabbits, rather than the nine rabbits of the original Draize test, but is otherwise substantially the same. While other tests have been proposed to replace the Draize test, none are widely used.

The Draize test, both in its original and modified forms, has been criticized on the basis of humane considerations, discrepancies in response between rabbit and human eyes, the subjective nature of the scoring system, and difficulties in interpreting test results because of interlaboratory variability on tests with identical materials. A review article by the Office of Pesticides and Toxic Substances of the United States Environmental Protection Agency and entitled "Eye Irritation Testing", EPA-560/11-82-001, discusses the Draize test, its modifications, and a number of the criticisms which have been made of the current methods of eye irritancy testing.

Accordingly, an object of the invention is to provide an in vitro method of testing the biocompatibility of a variety of substances and for use in lieu of in vivo testing.

Another object is to provide a method of testing ocular irritancy of a variety of substances without the use of laboratory animals.

A further object is to provide a test for ocular irritancy of substances which has a high correlation to effects on humans.

A still further object is to provide an improved in vitro method of toxicological testing.

These and other objects and features of the invention will be apparent from the following description and the drawing.

SUMMARY OF THE INVENTION

The present invention features an in vitro method of testing substances for biocompatibility with a specified mammalian tissue. The method is based on the ability of a confluent cell culture to repair damage in its structure after disruption of the sheet structure. Biocompatibility, particularly toxicological effect, is determined by observation of the change in repair rate of the culture after treatment with the substance being tested.

More specifically, the invention employs the preliminary step of providing a culture of confluent cells. While any confluent cell culture whose response can be correlated to the effect on the desired tissue can be used, mammalian cells, particularly confluent cell cultures formed of epithelial cells, e.g., rabbit or human corneal epithelial cells, are presently preferred. The confluent culture may be subdivided into smaller cultures for ease of testing. The use of corneal epithelial cells is particularly well adapted if the substance is being tested to determine the effect of ocular tissue.

According to the invention, a selected and repeatable disruption, e.g., of a specified nature and degree and having a specified shape and area, is produced in the confluent cell culture. One method of forming the disruption is by freezing a delineated portion of the cell culture, e.g., with a liquid nitrogen-treated probe. The method of freezing the cell cultures is particularly advantageous for causing this disruption since it produces the desired disruption in a clearly defined region.

The confluent cell culture is treated with the substance to be tested, to initiate the test. Normally, treatment is just after disruption of the culture, but occasionally the culture is treated with the material to be tested before disruption to determine a particular type of effect. The medium can be changed after treatment to modify the duration of exposure of the culture to the substance. For purpose of this procedure, treatment can be any means of exposing the culture to the substance being tested. The specific method of treatment varies depending on the properties of the substance.

The treated cell culture is then incubated under conditions which are known to promote closure of the disruption. Closure is affected by the migration and growth of cells of the confluent culture across the disruption. A standard is prepared by observing the degree of closure of the disruption at various times in an untreated culture and the biocompatibility of the substance is determined by comparing the degree of closure for the treated culture with the standard at a specified time or times after treatment. A determination of the level at which the substance inhibits or otherwise effects closure of the disruption is achieved by comparing the effects of different amounts of the substance, for example using serial dilutions. Normally, one runs controls or standards together with the test culture to determine whether there has been a problem with the incubation conditions. Controls are cell cultures which are identical to that used for testing except they are not disrupted and are not treated with the substance to be tested.

While the preferred tissue for testing biocompatibility of a substance is from the organ which would be exposed, it is not required. In any test procedure, a correlation is made between the results of the test and the in vivo reaction. For example, skin epithelial cells can be used in place of corneal epithelial cells to predict the toxicity on ocular tissue. In like manner, frog epithelial cells in place of mammalian cells can be used if a correlation is determined.

DESCRIPTION OF A PREFERRED EMBODIMENT

The present invention concerns a method for in vitro analysis of the biocompatibility of a variety of substances on mammalian tissue. The analysis involves a comparison of the degree of closure of a disruption in a confluent cell culture which has been treated with the substance of interest with the corresponding degree of closure for an untreated control culture. The test is particularly useful for showing toxicological effect and has excellent correlation with the effect on specified tissue.

Figure 1:
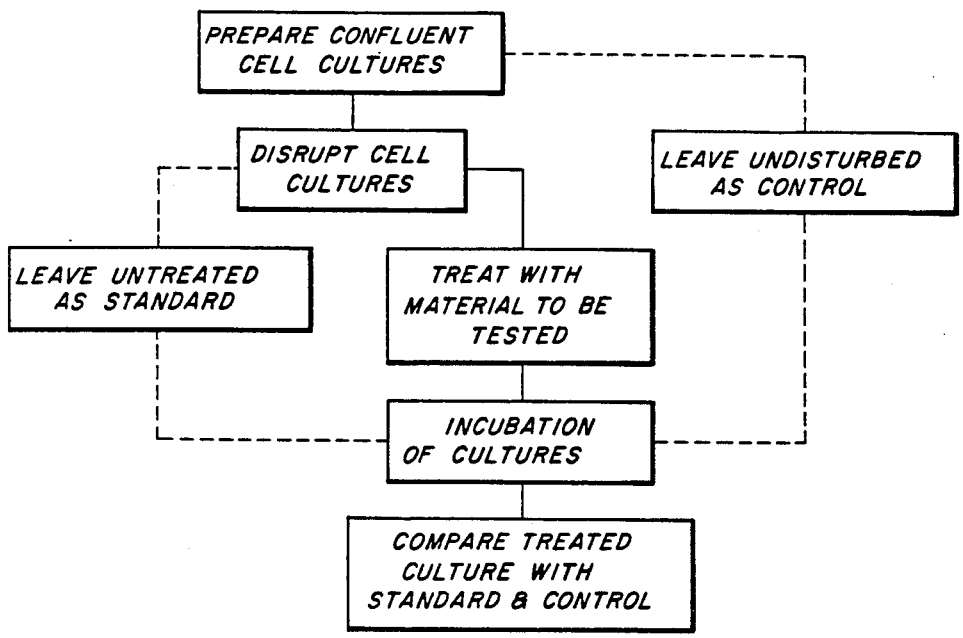
FIG. 1 is a flow chart of a method for practice of the invention.

FIG. 1 is a flow chart of a method for the practice of the invention. Briefly, a confluent cell culture is provided and a portion of the culture is disrupted, either before or shortly after treatment with the substance to be tested. Normally the disruption occurs before treatment as is illustrated in the Figure. Preferably, a plurality of cultures are used and each culture is treated with a different concentration of the substance to determine the level at which an identifiable effect is apparent. The disrupted cell cultures are incubated for a predetermined period of time and the degree of closure of the disruption is compared with a standard to determine if there is a toxicological effect. Time duration of exposure to the substance may be modified to parallel actual exposure conditions by changing the medium at predetermined intervals. Standards, which are disrupted but untreated, and controls, which are neither disrupted nor treated, are often included to ensure the validity of the test. The following Example illustrates the method of the invention.

EXAMPLE

The confluent cell culture in this Example is formed of rabbit corneal epithelial cells initiated from Dispase II treated corneas. The cultures are established in a medium consisting of equal parts of Dulbecco's Modified Eagles Medium and Hams F12 supplemented with 5% (v/v) fetal bovine serum, 0.1 g/ml of cholera toxin, 10 ng/l of epidermal growth factor, 5 g/ml of insulin, 5 g/ml of gentamycin, and 0.5% (v/v) dimethylsulfoxide. The epithelial cells are grown for 7-10 days and then plated into a 24-well multiplate. Each well contains 1 ml of the medium as described except the cholera toxin is omitted. Each well contains about $3 \times 10^4$ cells at test initiation. Each of the twenty-four wells constitutes a separate test culture. Four replicates are used, allowing six distinct experiments or test levels to proceed simultaneously.

The following procedure is used to cause the disruption of the individual cell cultures in the wells. Disks, 7 mm in diameter, are cut from Millipore HA filters, rinsed in six changes of distilled water, boiled in distilled water, and dried in a laminar flow hood. A disk is placed on the surface of each culture of the 24-well multiplate and gently tapped down. A stainless steel probe, which is also 7 mm in diameter, is cooled in liquid nitrogen, placed against the back plastic surface of the well directly opposite the disk, and held against the plastic surface of the disk for approximately 5 seconds. The probe is then removed and a medium consisting of Dulbecco's Modified Eagles Medium and Ham's F12 with the addition of gentamycin and dimethylsulfoxide is added. The disk is carefully lifted out using forceps, leaving a discrete, well-defined circular defect or disruption in the cell layer. The filter-like disk is provided to enhance the removal of damaged cells from the disrupted area, after inflicting the frozen probe on the cell culture. Hence, upon removal of the disk, the culture is essentially free of cellular debris throughout the disruption. The medium is preferably added, as stated, prior to removal of the disk, but may, instead, be added thereafter; the purpose is for cellular nourishment as conventional in culture practices.

Figure 2:
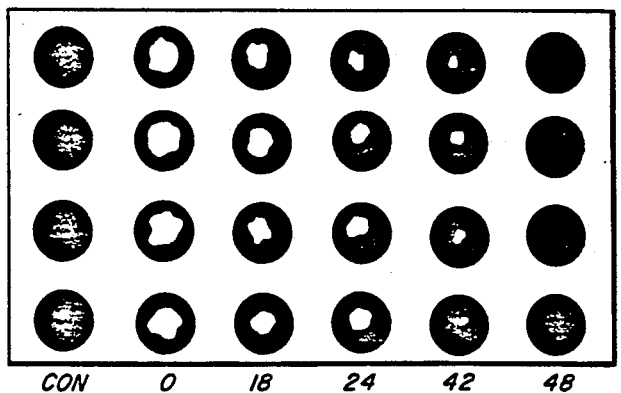
FIG. 2 is an illustration of a standard multi-well plate showing four replicates of wound closure at different times according to one practice of the invention.

According to one practice of the invention, the substance being tested is added to the medium at this time and the cell cultures are incubated. A control culture which is not exposed to the substance and not disrupted can be included to verify cell number and to ensure that a proper incubation has occurred. FIG. 2 shows the degree of wound disclosure for four sets of replicate wounds. The column marked CON are the controls and all of the numbers are hours after cell culture disruption. For rabbit corneal epithelial cells disrupted using this procedure (the cells used in the procedure shown in FIG. 2), complete closure takes approximately 48 hours.

It is unnecessary to wait 48 hours or until complete closure occurs to obtain results from the present test. At 24 hours, a substantial difference in closure is evident on fixed and stained cultures. The cell number of the control culture, which is determined to ensure proper incubation, will normally be greater than $1 \times 10^5$ cells/well at 24 hours. Grading of the disrupted cultures can take place visually but a computer-assisted area measuring apparatus, such as the Zeiss Videoplan Image Analysis System which digitizes and compares the area with a standard, has been found advantageous.

In order to determine the level of the substance which cause a toxicological effect, different amounts of the substance are tested by serial dilution. Two often used measures of biocompatibility are permissive and cytotoxic doses. The permissive dose is defined as the highest dose which does not show an effect of the treatment while the cytotoxic dose is defined as the lowest dose which completely inhibits closure, showing a killing of all the cells in the culture. This procedure allows easy determination of the permissive and cytotoxic doses.

As noted, the foregoing procedure features the use of the confluent cell culture. Epithelial cells, e.g., corneal epithelial cells, are confluent cultures particularly useful in the practice of the invention, but other confluent cell cultures may be used. The principal requirement for cell culture selection is that the disruption in the sheet-like structure of the cells closes, upon normal cell migration and growth, in the absence of the substance being tested for biocompatibility, and shows an observable effect upon treatment.

Freezing using a liquid nitrogen-cooled probe placed opposite a filter disk is the preferred method of disrupting the cell culture because the cells adhere to the disk allowing for ease of cell removal. However, other means of disrupting the culture may be used. These other methods include scraping a particular area out of the culture and treatment with a material such as heptanol which kills cells in a limited area.

Those skilled in the art may determine other methods which are modifications of variations of the procedures set forth herein. Such other methods are within the scope of the following claims.

What is claimed is:

1. A method of testing a substance for toxicological effect on a specified mammalian tissue, said method comprising the steps of
   preparing a culture of confluent cells,
   producing a selected and repeatable disruption in said confluent cell culture,
   treating said disrupted confluent cell culture with the substance to be tested for toxicological effect,
   incubating said treated cell culture to affect closure of said disruption, and
   determining the toxicological effect of said substance by comparing the relative degree of closure of said disruption with standards of disrupted confluent cell cultures.

2. A method according to claim 1 wherein said specified mammalian tissue comprises ocular tissue.

3. A method according to claim 1 wherein said standards comprise cultures of said confluent cells which are not treated with said material, said untreated cell cultures being disrupted and grown in a substantially identical manner to said treated cell culture.

4. A method according to claim 1 wherein said culture of confluent cells in said step comprises epithelial cells.

5. A method according to claim 1 wherein said culture of confluent cells comprises mammalian cells.

6. A method according to claim 5 wherein said confluent mammalian cells comprise corneal epithelial cells.

7. A method according to claim 6 wherein said corneal epithelial cells are selected from a group consisting of rabbit corneal epithelial cells and human corneal epithelial cells.

8. A method according to claim 1 wherein said step of determining toxicological effect of said substance comprises testing a plurality of amounts of said substance to determine an amount at which said substance inhibits closure of said disruption.

9. A method according to claim 8 wherein said determining step comprises testing serial dilutions of said substance to determine said amount.

10. A method according to claim 1 wherein said disruption producing step includes the step of producing a disruption having a specific size and shape in said cell culture.

11. A method according to claim 10 wherein said disruption producing step comprises the step of inflicting a specified freezing condition upon said size-delineated disruption area.

12. A method according to claim 9 wherein said freezing step comprises lowering the temperature of said area to the temperature of liquid nitrogen.

13. A method according to claim 11 wherein said disruption producing step includes contacting said cell culture with a probe having a selected sub-freezing temperature.

* * * * *

UNITED STATES PATENT AND TRADEMARK OFFICE
CERTIFICATE OF CORRECTION

PATENT NO. : 4,760,020
DATED : July 26, 1988
INVENTOR(S) : Arthur H. Neufled et al.

It is certified that error appears in the above-identified patent and that said Letters Patent is hereby corrected as shown below:

At Column 1, line 10 delete "toxcological" and insert --toxicological--.

At Column 2, line 32 delete "of" and insert --on--.

At Column 4, line 35 delete "disclosure" and insert --closure--.

Signed and Sealed this

Fourth Day of July, 1989

Attest:

DONALD J. QUIGG

Attesting Officer

Commissioner of Patents and Trademarks